(12) United States Patent
Sakon et al.

(10) Patent No.: US 7,655,123 B2
(45) Date of Patent: Feb. 2, 2010

(54) GAS SENSOR

(75) Inventors: Atsushi Sakon, Tokai (JP); Osamu Nakasone, Inabe (JP); Kaori Takahashi, Nagoya (JP); Toshihiko Suzuki, Nagoya (JP)

(73) Assignee: NGK Insulators, Ltd., Nagoya-shi (JP)

( * ) Notice: Subject to any disclaimer, the term of this patent is extended or adjusted under 35 U.S.C. 154(b) by 781 days.

(21) Appl. No.: 10/997,051

(22) Filed: Nov. 24, 2004

(65) Prior Publication Data

US 2005/0126910 A1   Jun. 16, 2005

(30) Foreign Application Priority Data

Nov. 27, 2003   (JP) .............................. 2003-398207

(51) Int. Cl.
*G01N 27/417*   (2006.01)
*G01N 27/409*   (2006.01)
*G01N 27/26*   (2006.01)

(52) U.S. Cl. ..................... 204/429; 204/424; 204/426; 204/428

(58) Field of Classification Search ......... 204/425–429, 204/424
See application file for complete search history.

(56) References Cited

U.S. PATENT DOCUMENTS

| | | | |
|---|---|---|---|
| 6,036,841 A * | 3/2000 | Kato et al. ................... 205/781 |
| 6,205,843 B1 * | 3/2001 | Tanaka et al. ............... 73/31.06 |
| 6,383,443 B1 * | 5/2002 | Jeng et al. .................... 264/621 |
| 7,169,724 B2 * | 1/2007 | Sakon et al. ................. 501/127 |
| 2003/0201171 A1 * | 10/2003 | Nakagaki et al. ....... 204/290.01 |
| 2003/0201172 A1 | 10/2003 | Nakagaki et al. |

FOREIGN PATENT DOCUMENTS

| | | |
|---|---|---|
| JP | 09-068515 | 3/1997 |
| JP | 2003-322636 | 11/2003 |

\* cited by examiner

*Primary Examiner*—Nam X Nguyen
*Assistant Examiner*—J. Christopher Ball
(74) *Attorney, Agent, or Firm*—Burr & Brown

(57) ABSTRACT

A gas sensor comprising a first measuring chamber for introducing a gas to be measured, a second measuring chamber for detection of the gas to be measured, and as pump cells a first pump cell having a pair of pump electrodes, and a second pump cell having a measuring electrode and an auxiliary pump electrode, wherein a porous alumina sintered body having communicating pores of 500-1100 Å in average pore diameter and 6-16% in porosity is formed as an electrode protective layer on the surface of at least the measuring electrode of the second pump cell in such a manner that the alumina sintered body covers the measuring electrode. The gas sensor can be use for long period of time because of the protective layer.

9 Claims, 6 Drawing Sheets

FIG.4
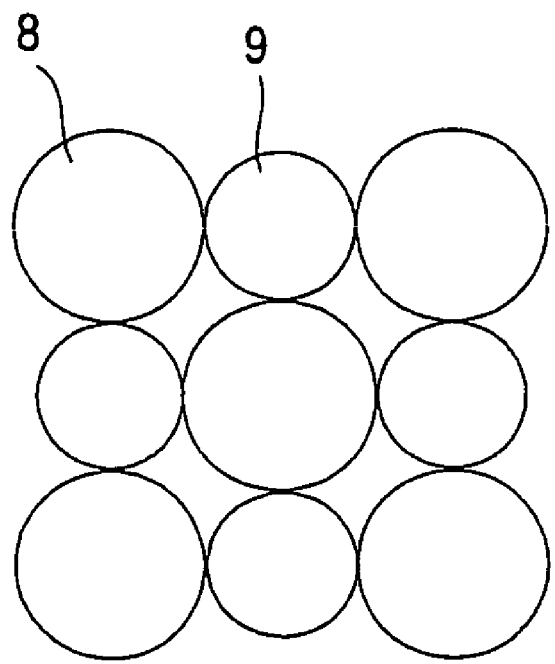
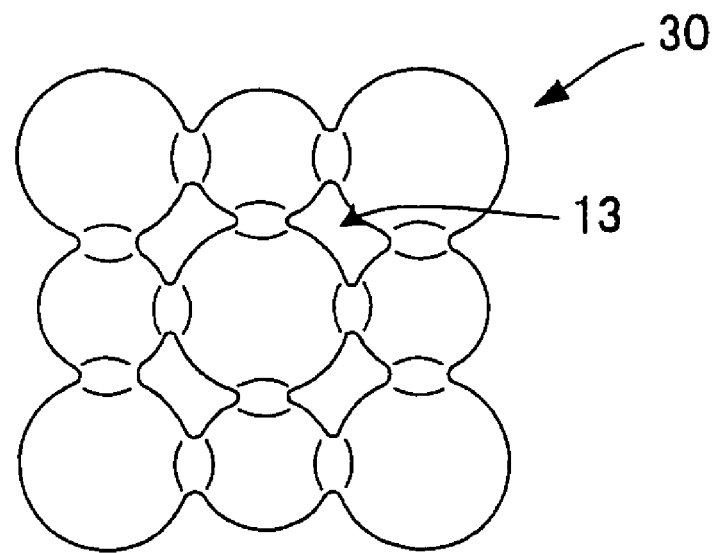

GAS SENSOR

CROSS REFERENCE TO RELATED APPLICATION

This application claims the benefit of Japanese Application 2003-398207, filed Nov. 27, 2003, the entirety of which is incorporated herein by reference.

BACKGROUND OF THE INVENTION

1. Field of the Invention

The present invention relates to a gas sensor, and, more particularly, to a gas sensor which can be inhibited from decrease in output of the gas to be measured at the time of detection and besides can attain stable output of the gas to be measured even after use of long time.

2. Description of the Prior Art

From the viewpoints of environmental protection such as inhibition of warming of the earth or inhibition of atmospheric pollution, gas sensors are used for detecting and measuring the concentration of various gases contained in exhaust gases discharged from internal combustion engines such as engines of automobiles, combustion exhaust gases discharged from combustion apparatuses such as combustion furnaces and incineration furnaces, e.g., oxygen ($O_2$), carbon monoxide (CO), carbon dioxide ($CO_2$), nitrogen ($N_2$), nitrogen oxides (NOx such as NO and $NO_2$) sulfur dioxide ($SO_2$), water ($H_2O$), etc.

The gas sensors include, for example, oxygen sensors used for measuring oxygen concentration in exhaust gases of automobiles to detect the combustion state in the engines (JP-A-9-68515). Recently, for the improvement of performance of automobiles, it is attempted not only to enhance performance of engines, but also to add various additives such as phosphorus, zinc, magnesium and calcium to engine oil or gasoline. However, if these additives mingle into exhaust gases, they stick to the surface of oxygen sensor to clog the communicating pores of the diffusion resistant layer or stick to the measuring electrode to deteriorate the electrode, resulting in reduction of output of the sensor or reduction of responsiveness.

Furthermore, there are NOx gas sensors for measuring NOx gas concentration in the exhaust gas in which the measuring electrode is protected with an electrode protective layer (JP-A-2003-322636). Porous alumina sintered bodies are generally as the electrode protective layers. The electrode protective layer has a function of diffusion regulating means for the gas to be measured. Moreover, since the measuring electrode is composed of an electrode material containing, for example, platinum (Pt) and rhodium (Rh) as main component metals, the measuring electrode made using an electrode material containing platinum (Pt) and rhodium (Rh) as main component metals has the problem of being poisoned with a slight amount of Au volatilized and scattered at a sintering step to cause considerable reduction of NOx gas decomposition activity, and hence an electrode protective layer comprising a porous alumina sintered body is formed on the surface of the measuring electrode.

The inventors have found that the NOx sensors have such an additional problem that during the use of them, gold (Au) volatilizes and scatters from an electrode of pump cell due to high temperature and sticks to the measuring electrode (e.g., a Pt—Rh electrode comprising platinum (Pt) and rhodium (Rh)) and reacts (poisons the measuring electrode) to cause deterioration of NOx gas decomposition activity (decrease in NOx gas output).

The porous alumina sintered body used as an electrode protective layer has been produced, for example, by preparing a paste comprising a mixture of an alumina powder as an aggregate and an aluminum salt as a pore forming material at a specific ratio, forming the paste into a desired shape and then sintering the formed body. When the alumina sintered body is used as an electrode protective layer for a measuring electrode of NOx gas sensors for detecting NOx gas in an exhaust gas discharged from automobiles, this is made by forming the prepared paste into a layer or thin film by screen printing and then sintering, and there are problems that variations occur in pore diameter and porosity of the resulting alumina sintered body (electrode protective layer), and NOx gas sensor of high accuracy cannot stably be made. Furthermore, since the input NOx gas must permeate the electrode protective layer, reach the measuring electrode and react to stably output the decomposed $N_2$ and $O^{2-}$, the layer is required to have uniform porosity higher than a specific value, and, besides, in order to inhibit the deterioration of NOx gas decomposition activity (reduction in NOx gas output) caused by penetration of gold (Au) volatilizing and scattering from the pump electrode through the electrode protective layer and sticking of the gold to the measuring electrode to cause reaction (poisoning of the measuring electrode), the layer is required to have a uniform pore diameter smaller than a specific value. In other words, the electrode protective layer is required to have intermediate physical properties between those of porous body and dense body.

FIG. 8 is a graph which shows relation between pore diameter (Å) of the electrode protective layer and Nox gas output reduction rate (%) which is an indicator for high-temperature endurance when a NOx gas sensor provided with a conventional electrode protective layer was continuously operated at 950° C. for 100 hours. As can be seen from FIG. 8, when the pore diameter of the electrode protective layer exceeds 1100 Å, the NOx gas output reduction rate (%) sharply increases.

SUMMARY OF THE INVENTION

However, there have not yet been obtained gas sensors in which pore characteristics such as pore diameter and porosity of communicating pores of the porous alumina sintered body are accurately controlled to the desired ranges and which can be inhibited from decreasing of output of the gas to be measured at the time of detection and besides can stably output the gas to be measured even after long-term use. The present invention has been accomplished in an attempt to solve the above problems, and the object of the present invention is to provide a gas sensor which can be inhibited from decreasing of output of the gas to be measured at the time of detection and besides can stably output the gas to be measured even after long-term use.

BRIEF DESCRIPTION OF THE DRAWINGS

FIG. 4 schematically shows behavior of aggregates and pore forming materials in the third production method (aggregate blending method) of the alumina sintered body as an electrode protective layer used in the embodiment.

Figure 1A:
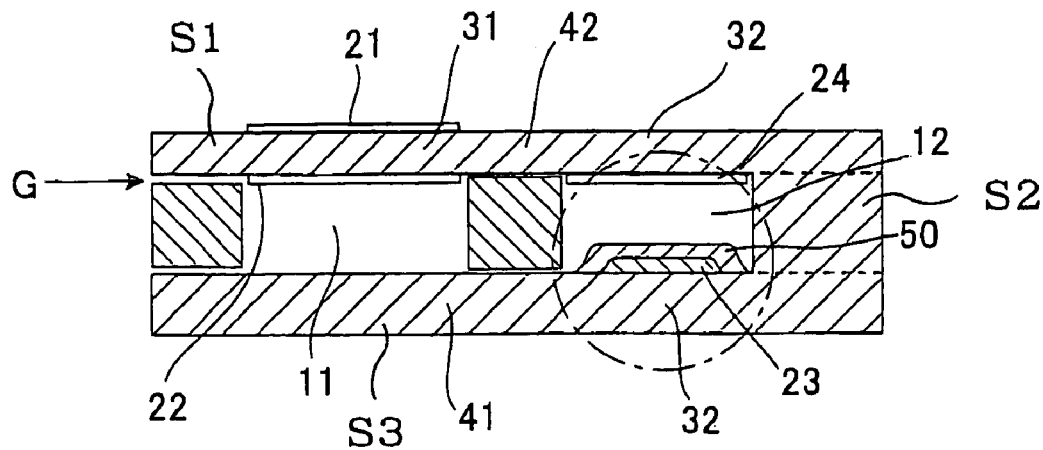
FIG. 1(*a*) is a sectional view which schematically shows one embodiment of the gas sensor of the present invention, and FIG. 1(*b*) is a partially enlarged view of the electrode protective layer in FIG. 1(*a*).

In the drawings, the reference numerals have the following meanings:

1 - - - The first alumina particles, 2 - - - The second alumina particles, 3 - - - Communicating pores, 4 - - - The third alumina particles, 5 - - - Sintering adjusting material, 6 - - - Sintering adjusting material bonding layer, 7 - - - Communicating pores, 8 - - - The fourth alumina particles, 9 - - - The fifth alumina particles, 10 - - - Alumina sintered body obtained by the first production method, 11 - - - The first measuring chamber, 12 - - - The second measuring chamber, 13 - - - Communicating pores, 20 - - - Alumina sintered body obtained by the second production method, 21 - - - Pump electrode, 22 - - - Pump electrode, 23 - - - Measuring electrode, 24 - - - Auxiliary pump electrode, 30 - - - Alumina sintered body obtained by the third production method, 31 - - - The first pump cell, 32 - - - The second pump cell, 41 - - - Substrate, 42 - - - Substrate, 50 - - - Electrode protective layer, 111 - - - The first measuring chamber, 112 - - - The second measuring chamber, 121 - - - Pump electrode, 122 - - - Pump electrode, 123 - - - Measuring electrode, 124 - - - Auxiliary pump electrode, 131 - - - The first pump cell, 132 - - - The second pump cell, 141 - - - Substrate, 142 - - - Substrate, G - - - Gas to be measured.

DETAILED DESCRIPTION OF THE INVENTION

In order to attain the above object, the present invention provides the following gas sensors.

(1) A gas sensor which has a diffusion regulating means for introduction of a gas to be measured and at least one pump cell having a pair of electrodes and which measures the concentration of the gas to be measured on the basis of a pump current passing through the pump cell, where a porous alumina sintered body having communicating pores of 500-1100 Å in average pore diameter and 6-16% in porosity is formed as an electrode protective layer on the surface of at least one of the pair of the electrodes of the pump cell to cover the measuring electrode. Here, "a porous alumina sintered body" means "a gas permeable alumina sintered body having communicating pores".

(2) A gas sensor described in the above (1), wherein the gas sensor has the diffusion regulating means for introduction of the gas to be measured and a first measuring chamber into which the gas to be measured is introduced through the diffusion regulating means and a second measuring chamber which detects the concentration of the gas to be measured, and further has as the pump cells a first pump cell having a pair of pump electrodes and a second pump cell having a measuring electrode; the oxygen concentration in the first measuring chamber is controlled to a specific value by the first pump cell in the first measuring chamber; the gas to be measured is reduced or decomposed in the second measuring chamber; and the concentration of the gas to be measured is measured on the basis of the second pump current passing through the second pump cell with the oxygen generated by the reduction or decomposition, and the porous alumina sintered body is formed as the electrode protective layer on the surface of the measuring electrode of the second pump cell to cover the measuring electrode.

(3) A gas sensor described in the above (1) or (2), wherein the pore distribution (distribution width of pore diameter) of the communicating pores in the alumina sintered body is 400-1100 Å.

(4) A gas sensor described in any one of (1) to (3), wherein the gas to be measured is a nitrogen oxide (NOx) gas.

According to the present invention, there are provided gas sensors which can be inhibited from decreasing of output of the gas to be measured at the time of detection and besides can stably output the gas to be measured even after long-term use.

Embodiments of the gas sensor of the present invention will be explained in detail below referring to the drawings.

The gas sensor of the present invention is a gas sensor which has a diffusion regulating means for introduction of a gas to be measured and at least one pump cell having a pair of electrodes and which measures the concentration of the gas to be measured on the basis of pump current passing through the pump cell, characterized in that a porous alumina sintered body having communicating pores of 500-1100 Å in average pore diameter and 6-16% in porosity is formed as an electrode protective layer on the surface of at least one of the pair of the electrodes of the pump cell in such a manner that it covers the measuring electrode. The gas sensor of the present invention is not particularly limited on the principle of detecting the gas, and specific construction such as the number, structure and disposition of the measuring chambers and pump cells, so long as it has pump cells and an electrode protective layer comprising an alumina sintered body having the above characteristics is formed on the surface of the measuring electrode.

Figure 1B:
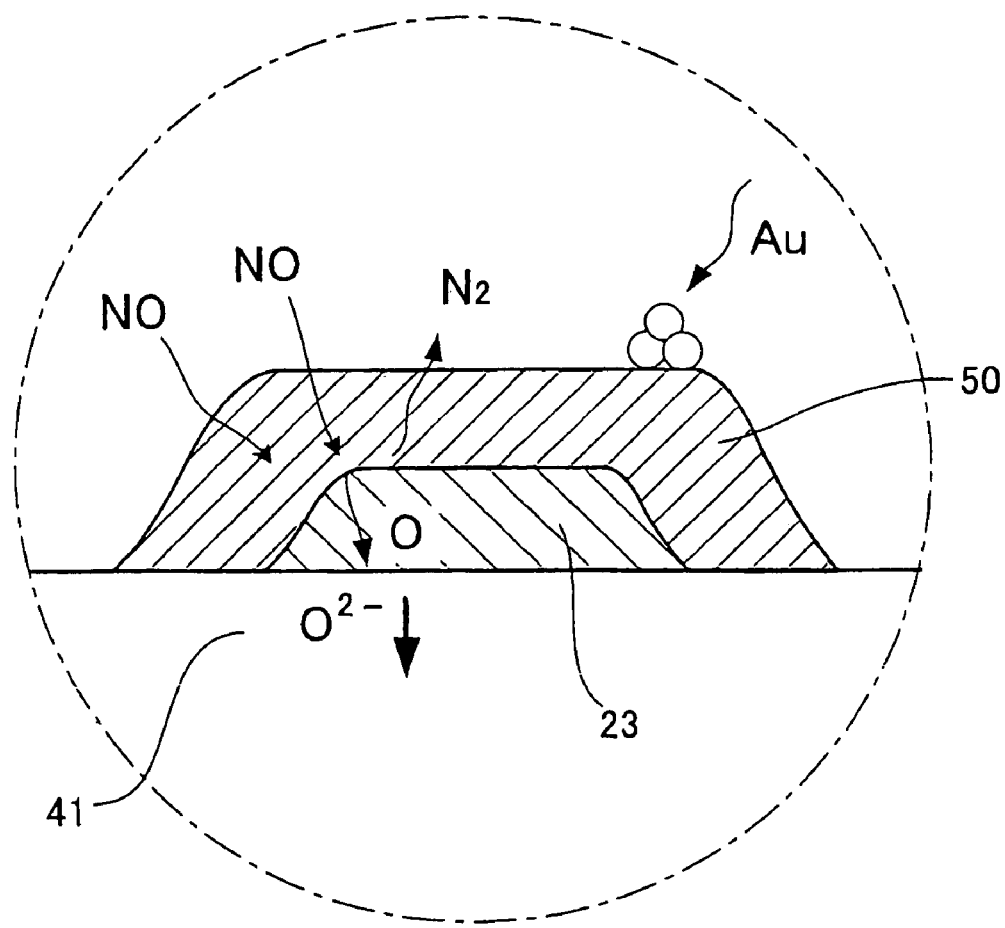

FIG. 1(a) is a sectional view which schematically shows one embodiment of the gas sensor of the present invention, and FIG. 1(b) is a partially enlarged view of the electrode protective layer in FIG. 1(a). As shown in FIG. 1(a) and FIG. 1(b), the gas sensor of this embodiment has a first measuring chamber 11 into which a gas G to be measured is introduced and a second measuring chamber 12 which detects the concentration of the gas G to be measured as measuring chambers, and, further, has a first pump cell 31 having a pair of pump electrodes 21 and 22 and a second pump cell 32 having a measuring electrode 23 and an auxiliary pump electrode 24 as pump cells, where oxygen is pumped out to such an extent that the gas G to be measured is not decomposed by the first pump cell 31 in the first measuring chamber 11, and the gas G to be measured is decomposed by the second pump cell 32 (measuring electrode 23) in the second measuring chamber 12, and the concentration of the gas G to be measured is measured on the basis of a second pump current passing through the second pump cell 32 by oxygen generated by the decomposition, and in this gas sensor, a porous alumina sintered body having communicating pores of 500-1100 Å, preferably 600-900 Å in average pore diameter and 6-16%, preferably 10-14% in porosity is formed as an electrode protective layer 50 on the surface of the measuring electrode 23 of the second pump cell 32 in such a manner that the alumina sintered body covers the measuring electrode 23. The measuring electrode 23 is disposed on the surface of a substrate 41 comprising, for example, zirconia ($ZrO_2$), cerium oxide ($CeO_2$), bismuth oxide ($Bi_2O_3$), or the like.

The gas to be measured in this embodiment is not particularly limited, and examples of the gas are oxygen ($O_2$), carbon monoxide (CO), carbon dioxide ($CO_2$), nitrogen ($N_2$), nitrogen oxides (NOx such as NO and $NO_2$), sulfur dioxide ($SO_2$), water ($H_2O$), etc. Among them, the gas sensor is effective for nitrogen oxide (NOx) gases.

As materials of the respective constituting elements used in this embodiment, mention may be made of, for example, Pt, Rh, Pd, etc. as the pump electrode 21, Pt—Au, Pt—Ag, etc. as the pump electrode 22, $Y_2O_3$—$ZrO_2$, $CeO_2$—$Y_2O_3$, $Bi_2O_3$—$Y_2O_3$, etc. as the first pump cell 31, Pt—Rh, Pt, Pd, etc. as the measuring electrode 23, Pt—Au, Pt—Ag, etc. as the auxiliary pump electrode 24, $Y_2O_3$—$ZrO_2$, $CeO_2$—$Y_2O_3$, $Bi_2O_3$—$Y_2O_3$, etc. as the second pump cell 32, and $Y_2O_3$—$ZrO_2$, $CeO_2$—$Y_2O_3$, $Bi_2O_3$—$Y_2O_3$, etc. as the substrates 41 and 42 which partition and constituting the first measuring chamber 11 and the second measuring chamber 12. In this embodiment, there are no particular limitations on the materials and structures of the constituting elements, the method for making the gas sensor, the method for fabrication of the gas sensor and the method for using the gas sensor, and there may be employed any of those which are generally employed, except for the electrode protective layer 50. For example, those which are disclosed in JP-A-10-46719, JP-A-2000-171438, JP-B-6-72861, etc. can be employed suitably.

The alumina sintered body as the electrode protective layer 50 used in this embodiment is a porous alumina sintered body obtained by sintering alumina particles as an aggregate in the presence of a pore forming material, and characterized in that the average particle diameter of the communicating pores is 500-1100 Å, preferably 600-900 Å, and the porosity thereof is 6-16%, preferably 10-14%. If the pore diameter is more than 1100 Å, high-temperature endurance is deteriorated and NOx gas output reduction rate (%) increases. If the porosity is higher than 16%, inflow rate of the NOx gas into the measuring electrode 23 increases and NOx gas output reduction rate (%) increases.

In this embodiment, the pore distribution (distribution width of pore diameter) of the communicating pores of the alumina sintered body is preferably 400-1100 Å, more preferably 600-900 Å. If the pore distribution is more than 1100 Å, the NOx gas output reduction rate (%) increases and, furthermore, the yield of NOx gas output is sometimes unstable.

The shape of the electrode protective layer (alumina sintered body) 50 in this embodiment is not particularly limited, and it may be in the form of, for example, a thin film or layer of 15-40 μm in thickness, a block, or the like.

The method for producing the electrode protective layer (alumina sintered body) used in this embodiment (the first to third production methods) will be explained.

Figure 2:
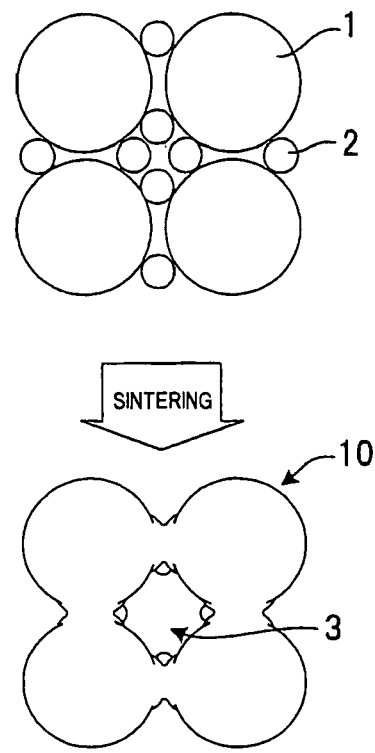
FIG. 2 schematically shows behavior of aggregates and pore forming materials in the first production method (interparticle embedding method) of the alumina sintered body as an electrode protective layer used in the embodiment.

As shown in FIG. 2, the first production method (hereinafter sometimes referred to as "interparticle embedding method") is a method for producing the alumina sintered body as the electrode protective layer which comprises mixing first alumina particles 1 having a particle diameter of 0.3-0.7 μm, preferably 0.4-0.5 μm and a sphericity of 0.7-1.0, preferably 0.8-1.0 as an aggregate and second alumina particles 2 having a particle diameter of 0.01-0.1 μm, preferably 0.01-0.05 μm as a pore forming material to embed a plurality of the second alumina particles 2 in the spaces between the first alumina particles 1, and sintering the mixture at a temperature of 1200-1400° C., preferably 1300-1380° C., thereby obtaining an alumina sintered body 10 in which the communicating pores 3 have an average pore diameter of 500-1100 Å, preferably 600-900 Å and a porosity of 6-16%, preferably 10-14%. The term "sphericity" is shown by r1/r2 in which r1 is a minor diameter of an ellipse and r2 is a major diameter of an ellipse. Therefore, when "r1/r2" is 1, it means the true sphere. This definition will be applied hereinafter.

If the particle diameter of the first alumina particles 1 is outside the range of 0.3-0.7 μm, and the sphericity is higher than 0.7, cohesiveness of the first alumina particles 1 increases, resulting in variations in pore diameter and porosity of the alumina sintered body 10 obtained by the sintering.

If the particle diameter of the second alumina particles 2 is outside the range of 0.01-0.1 μm, the sintering degree of the second alumina particles 2 at the time of sintering is outside the preferred range, resulting in variations in pore diameter and porosity of the alumina sintered body 10 obtained by the sintering. In this sense, the sphericity of the second alumina particles 2 is also preferably 0.7-1.0, more preferably 0.8-1.0. Furthermore, if the sintering temperature is outside the range of 1200-1400° C., the sintering becomes insufficient or excessive, and the necessary pore characteristics cannot be obtained.

In the first production method, the pore distribution (distribution width of pore diameter) of the resulting alumina sintered body 10 is preferably 400-1100 Å, more preferably 600-900 Å. If the pore distribution is greater than the upper limit of this range, the electrode activity is deteriorated by the poisoning substances.

The first alumina particles 1 and the second alumina particles 2 are not particularly limited so long as they have the particle diameter and sphericity within the above ranges and have uniform particle diameter and uniform shape, and examples of the alumina particles are α-alumina, γ-alumina, and the like.

As a specific method for mixing the first alumina particles 1 and the second alumina particles 2 to embed a plurality of the second alumina particles 2 in the spaces between the first alumina particles 1 and forming the layer on the measuring electrode (not shown), mention may be made of, for example, a method of coating a slurry prepared by dispersing the mixed alumina in an organic binder solution. In this case, the mixing ratio of the first alumina particles 1 and the second alumina particles 2 is such that the second alumina particles 2 are mixed in an amount of preferably 0.3-1.5% by mass, more preferably 0.5-1.0% by mass based on the first alumina particles 1.

The sintering method is not particularly limited, and there is a method of, for example, heating the coated film in the atmosphere.

In the present invention, the particle diameter, sphericity, pore diameter, porosity and pore distribution (distribution width of pore diameter) can be measured as mentioned below.

The particle diameter is measured using a laser diffraction type particle size distribution measuring apparatus according to a particle size distribution measuring method, the sphericity is calculated from an SEM photograph of the particles, and the pore diameter, porosity and pore distribution are measured by a mercury porosimeter.

Figure 3:
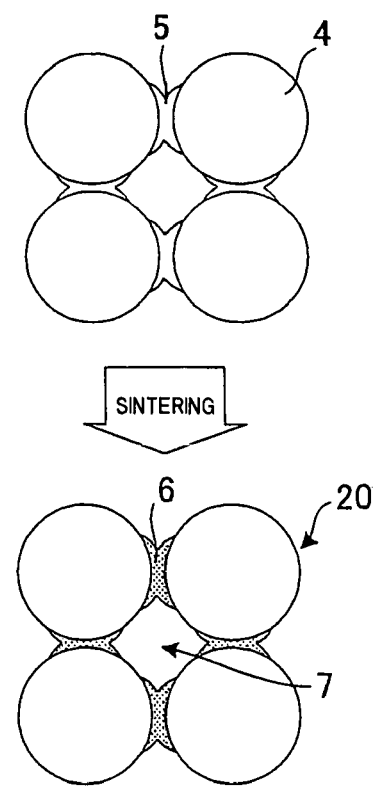
FIG. 3 schematically shows behavior of aggregates and pore forming materials in the second production method (interparticle bonding method) of the alumina sintered body as an electrode protective layer used in the embodiment.

As shown in FIG. 3, the second production method (hereinafter sometimes referred to as "interparticle bonding method") is a method for producing an alumina sintered body as an electrode protective layer which comprises sintering third alumina particles 4 having a particle diameter of 0.3-0.7 µm, preferably 0.4-0.5 µm and a sphericity of 0.7-1.0, preferably 0.8-1.0 as an aggregate at a temperature of 1200-1400° C., preferably 1300-1380° C. in the presence of a sintering adjuster 5 containing silicon dioxide ($SiO_2$) and magnesium oxide (MgO) as a pore forming material to bond the third alumina particles 4 to each other through a layer of the sintering adjuster 5 (sintering adjuster bonding layer 6), thereby obtaining an alumina sintered body 20 in which the communicating pores 7 have an average pore diameter of 500-1100 Å, preferably 600-900 Å and a porosity of 6-16%, preferably 10-14%.

If the particle diameter of the third alumina particles 4 is outside the range of 0.3-0.7 µm, and the sphericity is outside the range of 0.7-1.0, cohesiveness of the third alumina particles 4 increases or the sintering degree becomes insufficient, resulting in variations in pore diameter and porosity of the alumina sintered body 20 obtained by the sintering.

The sintering adjuster 5 is not particularly limited so long as it contains silicon dioxide ($SiO_2$) and magnesium oxide (MgO), and as examples, mention may be made of $SiO_2$+MgO+CaO and $SiO_2$+MgO+BaO. The sintering adjuster 5 is mixed in an amount of preferably 0.02-2% by mass, more preferably 0.05-1% by mass based on the third alumina particles 4.

In the second production method, the pore distribution (distribution width of pore diameter) of the alumina sintered body 20 obtained is preferably 400-1100 Å, more preferably 500-900 Å. If the pore distribution is greater than the upper limit in this range, the electrode activity is deteriorated by poisoned materials.

The third alumina particles 4 are not particularly limited so long as they have the particle diameter and sphericity in the above ranges and have uniform particle diameter and uniform shape, and examples of the alumina particles are α-alumina, γ-alumina, and the like.

As a specific method for mixing the third alumina particles 4 with the sintering adjuster 5 and bonding the third alumina particles 4 to each other through a layer of the sintering adjuster 5 (sintering adjuster bonding layer 6) to form the layer on the measuring electrode (not shown), mention may be made of, for example, a method of coating a slurry prepared by dispersing the mixture of the alumina and the sintering adjuster components in an organic binder solution.

As shown in FIG. 4, the third production method (hereinafter sometimes referred to as "aggregate blending method") is a method for producing an alumina sintered body as an electrode protective layer which comprises mixing fourth alumina particles 8 having a particle diameter of 0.4-1.0 µm, preferably 0.5-0.7 µm and a sphericity of 0.7-1.0, preferably 0.8-1.0 as an aggregate and fifth alumina particles 9 having a particle diameter of 0.2-0.8 µm, preferably 0.3-0.5 µm as a pore forming material to insert the fifth alumina particles 9 into the spaces between the fourth alumina particles 8, and sintering the mixture at a temperature of 1200-1400° C., thereby obtaining an alumina sintered body 30 in which the communicating pores 13 have a pore diameter of 500-1100 Å, preferably 600-900 Å and a porosity of 6-16%, preferably 10-14%.

If the particle diameter of the fourth alumina particles 8 is outside the range of 0.4-1.0 µm and the sphericity is outside the range of 0.7-1.0, cohesiveness of the fourth alumina particles 8 increases or the sintering degree becomes unstable, resulting in variations in pore diameter and porosity of the alumina sintered body 30 obtained by the sintering.

If the particle diameter of the fifth alumina particles 9 is outside the range of 0.2-0.8 µm, the sintering degree of the fifth alumina particles 9 at the time of sintering is outside the preferred range, resulting in variations in characteristics such as pore diameter and porosity of the alumina sintered body 30 obtained by the sintering. In this sense, the sphericity of the fifth alumina particles 9 is also preferably 0.7-1.0, more preferably 0.8-1.0. Furthermore, if the sintering temperature is outside the range of 1200-1400° C., the sintering becomes insufficient or excessive, and the necessary pore characteristics cannot be obtained.

In the third production method, the pore distribution (distribution width of pore diameter) of the alumina sintered body 30 obtained is preferably 400-1100 Å, more preferably 600-900 Å. If the pore distribution is greater than the upper limit in this range, there occurs deterioration in electrode activity due to poisoned materials.

The fourth alumina particles 8 and the fifth alumina particles 9 are not particularly limited so long as they have the particle diameter and sphericity within the above ranges and have uniform particle diameter and uniform shape, and examples of the alumina particles are α-alumina, γ-alumina, and the like.

As a specific method for mixing the fourth alumina particles 8 and the fifth alumina particles 9 to insert the fifth alumina particles 9 in the spaces between the fourth alumina particles 8 to form a layer on the measuring electrode (not shown), mention may be made of, for example, a method of coating a slurry prepared by dispersing the mixed alumina in an organic binder solution. In this case, the mixing ratio of the fourth alumina particles 8 and the fifth alumina particles 9 is such that the fifth alumina particles 9 are mixed in an amount of preferably 50-90% by mass, more preferably 70-90% by mass based on the fourth alumina particles 8.

The difference between the first production method (interparticle embedding method) and the third production method (aggregate blending method) resides in the size of the alumina particles 2 and that of the alumina particles 9.

EXAMPLE

The present invention will be explained specifically by the following production examples, examples, comparative production examples and comparative examples, which should not be construed as limiting the invention in any manner.

Production Example 1

First, an electrode protective layer (alumina sintered body) was produced in the following manner.

Example of production by the first production method:

To a raw material powder comprising the first alumina particles 1 was added a slurry containing a dispersion medium (e.g., ethanol), a dispersant and the second alumina particles 2, followed by premixing them. Then, to the mixture was added a solution (hereinafter referred to as "organic binder solution") prepared by previously dissolving an organic binder (e.g., ethyl cellulose) and a plasticizer in a solvent (e.g., terpineol), followed by further mixing them, and the viscosity of the mixture was adjusted by removing the dispersion medium and further adding the solvent to obtain a paste.

Production Example 2

Example of production by the second production method:

To a raw material powder comprising the third alumina particles 4 were added a dispersion medium (e.g., ethanol), a dispersant, a source of $SiO_2$ (e.g., silica sol) and a source of MgO (e.g., magnesium acetate), and a paste was obtained by carrying out the same subsequent procedures as in the above first production method of the Production Example 1.

Production Example 3

Example of production by the third production method:

To a mixture of a raw material powder comprising the fourth alumina particles 8 and a raw material powder comprising the fifth alumina particles 9 were added a dispersion medium (e.g., ethanol) and a dispersant, and a paste was obtained by carrying out the same subsequent procedures as in the above first production method of the Production Example 1.

Comparative Production Example 1

Example of production by a conventional production method:

To a mixture of a raw material powder comprising conventional alumina particles and an aluminum salt (e.g., aluminum hydroxide) were added a dispersion medium (e.g., ethanol) and a dispersant, and a paste was obtained by carrying out the same subsequent procedures as in the above first production method of the Production Example 1.

(Evaluation of Alumina Sintered Body)

Table 1 shows particle diameter, shape, mixing ratio and sintering temperature of the materials (aggregate and pore forming material) used in Production Examples 1-3 and Comparative Production Example 1, and pore diameter, porosity and pore distribution (distribution width of pore diameter) of the alumina sintered bodies obtained in Production Examples 1-3 and Comparative Production Example 1. As shown in Table 1, the pore diameter, porosity and pore distribution (distribution width of pore diameter) of the alumina sintered bodies obtained in Production Examples 1-3 were more accurately controlled than those of the alumina sintered body obtained in Comparative Production Example 1.

TABLE 1

|  | Production Example 1 | Production Example 2 | Production Example 3 | Comparative Production Example 1 |
|---|---|---|---|---|
| Particle diameter of aggregates (μm) | 0.4 | 0.4 | 0.4 & 0.5 | 0.2 |
| Shape of aggregates (sphericity) | 0.85 | 0.85 | 0.9 & 0.85 | 0.6 |
| Mixing ratio (amount of addition) | 0.5 wt. % of particles having size of 0.01 μm | 0.06 wt. % of MgO + $SiO_2$ | 0.4 μm: 80 wt. % 0.5 μm: 20 wt. % | 7 wt. % of aluminum hydroxide |
| Sintering temperature (° C.) | 1365 | 1365 | 1365 | 1365 |
| Average pore diameter (Å) | 720 | 590 | 720 | 850 |
| Porosity (%) | 8 | 11 | 9 | 16 |
| Distribution width of pores (Å) | 500~900 | 400~800 | 500~900 | 500~1100 |

Figure 5:
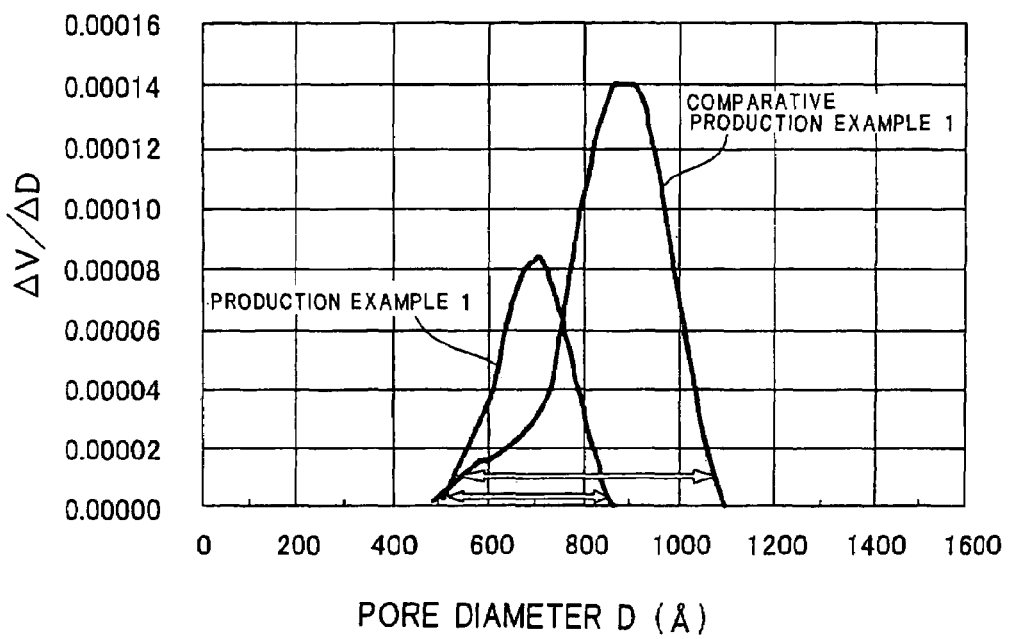
FIG. 5 is a graph which shows a comparison on pore distribution (distribution width of pore diameter) of the alumina sintered body obtained in Production Example 1 and that of the alumina sintered body obtained in Comparative Production Example 1.

FIG. 5 shows a comparison on the pore distribution (distribution width of pore diameter) of the alumina sintered body obtained in Production Example 1 and the alumina sintered body obtained in Comparative Production Example 1. As can be seen from FIG. 5, the pore distribution (distribution width of pore diameter) of the alumina sintered body obtained in Production Example 1 was about ½ of the pore distribution of the alumina sintered body obtained in Comparative Production Example 1.

Example 1

Production of Element:

A paste which forms pump electrode 21 was printed on the upper surface of a zirconia (solid electrolyte) sheet S1, and a paste which forms pump electrode 21 and auxiliary pump electrode 24 was printed on the under surface of the sheet S1. Furthermore, a paste which forms a measuring electrode 83 was printed on the upper surface of a zirconia (solid electrolyte) sheet S3, followed by printing a paste for the formation of electrode protective layer 50 which was prepared so as to obtain the same sintered body as the alumina sintered body obtained in Production Example 1. Then, a punched zirconia (solid electrolyte) sheet S2 interposed between the zirconia (solid electrolyte) sheet S1 and the zirconia (solid electrolyte) sheet S3 which had been subjected to the printing, thereby to form a space between the sheets S1 and S3, and the resulting laminate was subjected to cutting and sintering. In this case, an organic paste (binder solution) was coated on a part of the sheet S2 and dried, and thereafter the organic paste was removed at the sintering step, thereby to form gas inflow passages between the sheet S1 and the sheet S2 and between the sheet S2 and the sheet S3.

Comparative Example 1

An element was produced in the same manner as in Example 1, except that there was used a paste for the formation of electrode protective layer 50 which was prepared so as to obtain the same sintered body as the alumina sintered body obtained in Comparative Production Example 1.

Evaluation of characteristics of the element:

The element obtained by the above method was set in a measurement cell, followed by passing a mixed gas of $N_2$, $O_2$ and NO having a given NO gas concentration under the condition of 700-800° C., and a current value corresponding to the NO gas concentration was output.

Figure 6:
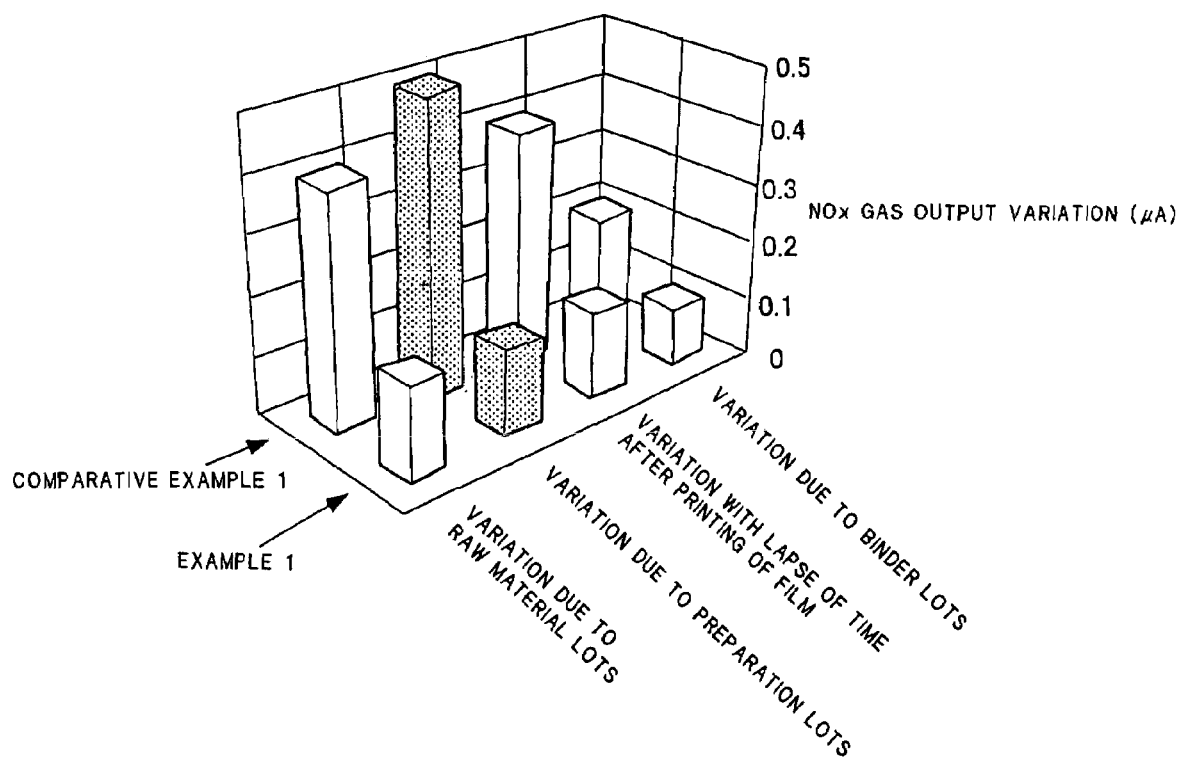
FIG. 6 is a graph which shows comparison on variation due to binder lots, variation with lapse of time after printing of film, variation due to preparation lots, and variation due to raw material lots in the gas sensor obtained in Example 1 and the gas sensor obtained in Comparative Example 1.

FIG. 6 shows comparisons on variation due to binder lots, variation with lapse of time after printing of film, variation due to preparation lots, and variation due to raw material lots in the gas sensors (Example 1) using the alumina sintered body as an electrode protective layer obtained in Production Example 1 and the gas sensor (Comparative Example 1) using the alumina sintered body as an electrode protective layer obtained in Comparative Production Example 1. As can be seen from FIG. 6, the gas sensor obtained in Example 1 was smaller in NOx gas output variation (μA) than the gas sensor obtained in Comparative Example 1.

Figure 7:
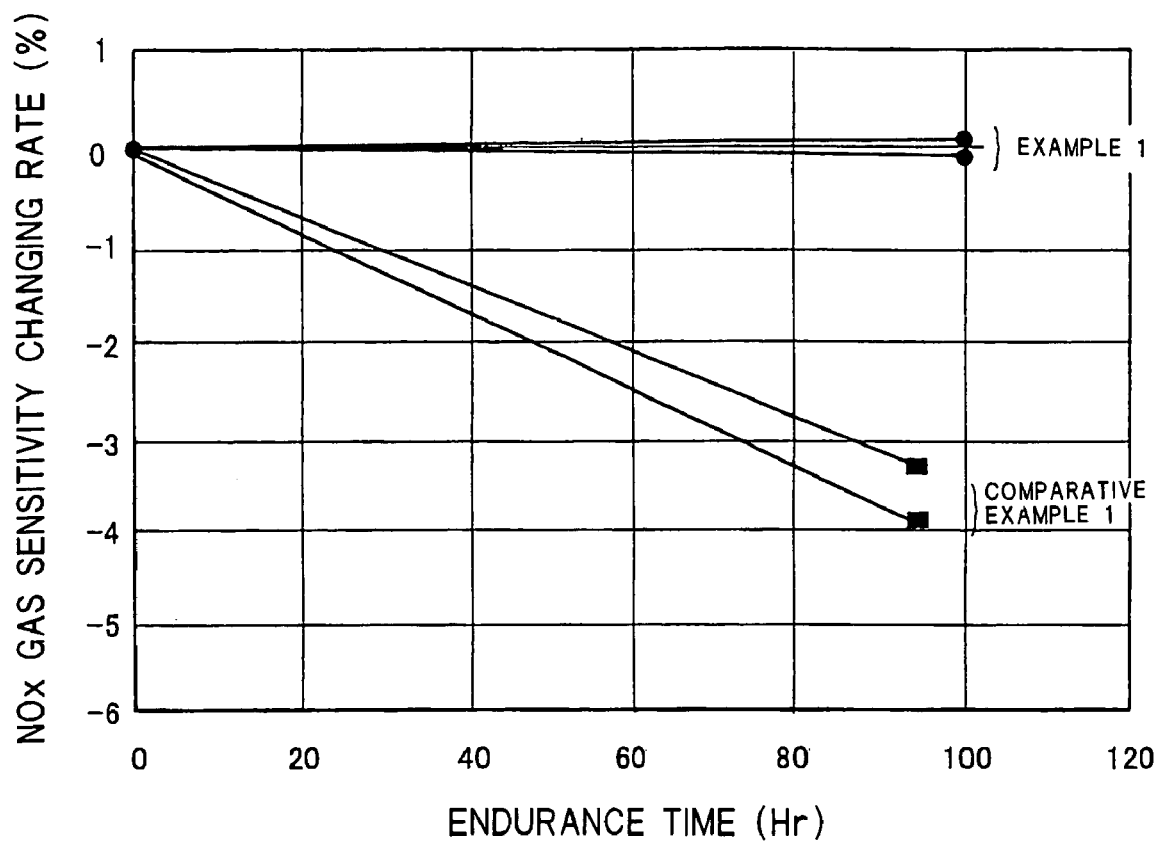
FIG. 7 is a graph which shows comparison of the results in continuous endurance test at 950° C. on the gas sensor obtained in Example 1 and the gas sensor obtained in Comparative Example 1.
Figure 8:
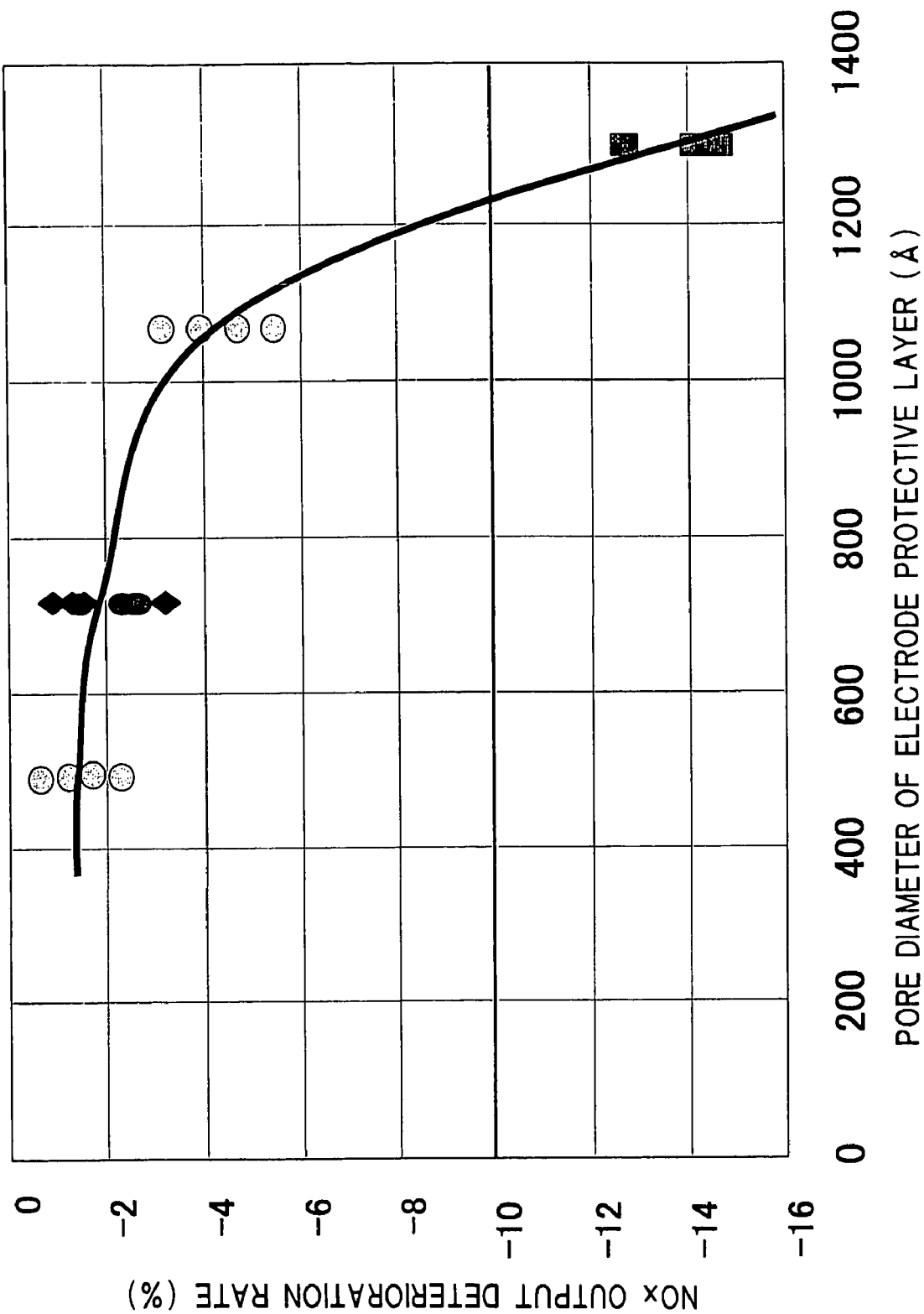
FIG. 8 is a graph which shows relation between pore diameter (Å) of the electrode protective layer and Nox gas output reduction rate (%) which is an indicator for high-temperature endurance (degree of poisoning with gold (Au) volatizing or scattering from an auxiliary pump electrode, or the like) when a NOx gas sensor provided with a conventional electrode protective layer was continuously operated at 950° C. for 100 hours.

FIG. 7 shows comparison on the results in continuous endurance test at 950° C. on the gas sensor (Example 1) using the alumina sintered body as an electrode protective layer obtained in Production Example 1 and the gas sensor (Comparative Example 1) using the alumina sintered body as an electrode protective layer obtained in Comparative Production Example 1. As can be seen from FIG. 7, the gas sensor obtained in Example 1 was smaller in NOx gas sensitivity changing rate (%) than the gas sensor obtained in Comparative Example 1.

The gas sensors of the present invention are effectively used as apparatuses for measuring concentrations of various gases contained in exhaust gases discharged from internal combustion engines such as engines of automobiles, combustion exhaust gases discharged from combustion apparatuses such as combustion furnaces and incineration furnaces, or contained in the atmosphere.

What is claimed is:

1. A gas sensor which has a diffusion regulating means for introduction of a gas to be measured, a first measuring chamber including a first pump cell comprising a first pair of pump electrodes, and a second measuring chamber including a second pump cell comprising a measuring electrode, wherein the gas to be measured is introduced into the first measuring chamber through the diffusion regulating means and a portion of the gas to be measured is introduced from the first measuring chamber into the second measuring chamber and is reduced or decomposed by the measuring electrode in the second measuring chamber, wherein the second pump cell measures the concentration of the gas to be measured on the basis of a pump current passing through the second pump cell, said gas sensor further comprising an electrode protective layer formed only on the surface of the measuring electrode of the second pump cell to cover the measuring electrode, said electrode protective layer comprising a porous alumina sintered body that includes alumina particles bonded together by a sintering adjuster bonding layer containing silicon dioxide and magnesium oxide so as to form communicating pores of 500-1100 Å in average pore diameter and 6-16% in porosity in said porous alumina sintered body.

2. A gas sensor according to claim 1, wherein an oxygen concentration in the first measuring chamber is controlled to a specific value by the first pump cell in the first measuring chamber and the second pump current passing through the second pump cell is generated by the reduction or decomposition of the gas to be measured in the second measuring chamber.

3. A gas sensor according to claim 1, wherein the pore distribution of the communicating pores in the alumina sintered body is 400-1100 Å.

4. A gas sensor according to claim 2, wherein the pore distribution of the communicating pores in the alumina sintered body is 400-1100 Å.

5. A gas sensor according to claim 1, wherein the gas to be measured is a nitrogen oxide gas.

6. A gas sensor according to claim 2, wherein the gas to be measured is a nitrogen oxide gas.

7. A gas sensor according to claim 3, wherein the gas to be measured is a nitrogen oxide gas.

8. A gas sensor according to claim 4, wherein the gas to be measured is a nitrogen oxide gas.

9. A gas sensor which has a diffusion regulating means for introduction of a gas to be measured, a first measuring chamber including a first pump cell comprising a first pair of pump electrodes, and a second measuring chamber including a second pump cell comprising a measuring electrode, wherein the second pump cell measures the concentration of the gas to be measured on the basis of a pump current passing through the second pump cell, said gas sensor further comprising a porous alumina sintered body having communicating pores of 500-1100 Å in average pore diameter and 6-16% in porosity formed as an electrode protective layer on the surface of at least the measuring electrode of the second pump cell to cover the measuring electrode, wherein the porous alumina sintered body has a thickness of 15 microns to 40 microns and includes alumina particles bonded together by a sintering adjuster bonding layer containing silicon dioxide and magnesium oxide.

* * * * *